United States Patent
Giacobbe et al.

[11] 3,963,581
[45] June 15, 1976

[54] AIR LIFT FERMENTORS

[75] Inventors: Francesco Giacobbe; Giampiero Longobardi, both of Rome, Italy

[73] Assignee: Compagnia Tecnica Industrie Petrolie S.p.A., Rome, Italy

[22] Filed: Feb. 24, 1975

[21] Appl. No.: 552,361

[30] Foreign Application Priority Data
Mar. 1, 1974 Italy .................................. 48801/74

[52] U.S. Cl. ............................................. 195/142
[51] Int. Cl.² .......................................... C12B 1/16
[58] Field of Search ............................. 195/142, 109

[56] References Cited
UNITED STATES PATENTS
3,400,051  9/1968  Hofschneider ..................... 195/142

*Primary Examiner*—Alvin E. Tanenholtz
*Attorney, Agent, or Firm*—Olson, Trexler, Wolters, Bushnell & Fosse, Ltd.

[57] ABSTRACT

An air lift fermentor comprising in combination a hollow cylindrical body, vertically located and subdivided into three zones by a pair of diaphragms parallel to the axis of said cylindrical body, the central zone of which is destined to fermentation of the liquor, and the two lateral zones serve for recirculating the liquor itself, after its passage through a heat exchanger and an air distributor, both located near the bottom of said cylindrical body.

6 Claims, 8 Drawing Figures

AIR LIFT FERMENTORS

The present invention relates to an improvement in the air lift fermentors where the air is either enriched or non-enriched with oxygen.

The air lift fermentors are those wherein the power necessary to obtain the required degree of mixing of the air with the fermentation liquor is supplied by the sole action of the air used for the fermentation.

The use of air lift fermentors proved to be very interesting for large mass plants, when due to the dimensions themselves, the use of an external mechanical stirring becomes problematic and expensive, and said air lift fermentors appeared to have a convenient practical utility for those fermentations requiring a high and constant aeration degree and wherein the liquors have suitable rheological characteristics (non high apparent density).

The air lift fermentors can be either of the natural circulation type or of the forced circulation type. In the forced circulation fermentors the re-circulation of the liquor lifted by the air is obtained by external mechanical power (- the recirculated liquor is pumped), while in the natural circulation fermentors the recirculation is obtained by a gradient of apparent density generated by the lifting action of the air.

Air lift fermentors have been embodied up to now of the forced circulation type and of the natural circulation type. In both said types, the refrigeration of the liquor as necessary for balancing the heat developed by the fermentation has been obtained up to now by the use of a refrigerator external to the fermentor itself. The refrigerator forms, therefore, an element separate from the main body of the fermentor, and is connected thereto by an external system of recirculation pipes.

According to this invention, a fermentor, of the air lift and natural recirculation type, is provided, having the features of: embodying the recirculation inside the fermentor itself with no aid of outer pipes, and by the sole and suitable arrangement of diaphragms inside the apparatus, and obtaining the cooling of the fermentation liquor by a heat exchanger located inside the fermentor itself.

This invention will be now described with reference to the attached drawings, showing by way of non limitative example, one preferred embodiment of the invention itself.

Figure 1:
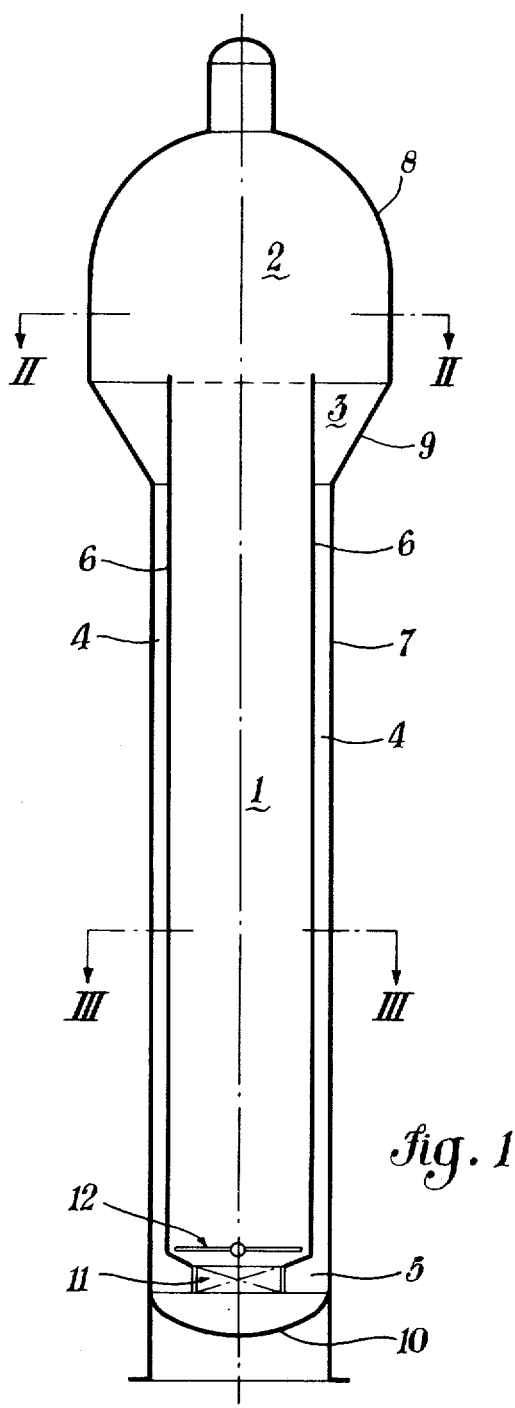
FIG. 1 is a diagrammatic longitudinal sectional view of the fermentor according to this invention.
Figure 2:
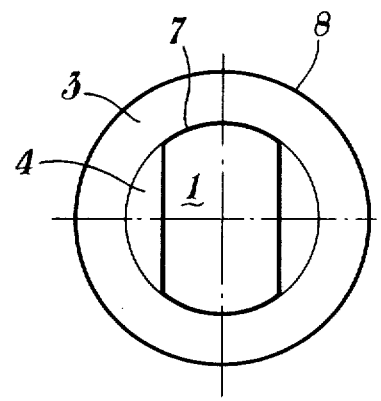
FIGS. 2 and 3 show the cross sectional views taken along the planes II—II and III—III of FIG. 1.
Figure 3:
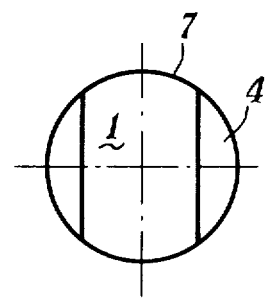

With reference to the FIGS. 1 to 3, the numeral reference 1 denotes the fermentation zone, defined by two parallel diaphragms 6 vertically located inside the cylindrical skirt 7 of the fermentor.

At the top there is a dome 8 having a cross section sensibly greater than that of the cylindrical body 7, and connected thereto by the frustoconical wall 9 which together with the diaphragms 6, defines the deaeration zone 3 communicating at its top with the zone 2 of gas-liquid separation, and at its bottom with the two spaces 4 forming the recirculation zone.

Near the bottom 10 of the body 7 there is a heat exchange unit 11 and an air distributor 12 which will be described in detail later on.

The operation is as follows:

In the fermentation zone 1 the liquor is lifted and powerfully mixed by the air which is fed through the distributor 12 located at the base of the same zone, just above the heat exchange zone 5.

The air outflows from the distributor at high speed and gives the liquor the power as necessary for its lifting and mixing. As immediate consequence of this action of the air, a difference of apparent density will be established between the aerated liquor, in the fermentation zone 1, and the non aerated liquor in the deaeration zone 3, and in the re-circulation zone 4, such as to allow the natural circulation of the liquor from the non aerated zones 3 and 4 to the aerated zone 1, through the heat exchange unit 11.

Within the zone 1 the chemical-biological transformations concerned with the fermentation occur, accompanied by development of heat which must be removed in order to maintain the temperature at its optimum operating value. This heat is removed in the heat exchange zone 5.

The air and the lifted liquor move upward under powerful mixing conditions through the fermentation zone 1 until reaching the top as established by the overflowings for feeding the deaeration zone 3. The liquor overfalls into the deaeration zone 3, while the exhausted air continues its upwards movement towards the zone 2 where as a consequence of the slowing due to the broadening of the cross sectional area and of the centrifugal separators, when issuing from the fermentor, said air leaves separate the liquor drops therein entrained.

When issuing from the fermentation zone 1, the liquor overfalls into the deaeration zone 3 where the air bubbles which remained contained in the liquor have the time and the way for becoming free, and then the liquor passes through the recirculation zone 4, and through the heat exchange zone 5 coming then again to the fermentation zone 1. In the heat exchange zone 5 is located the tube nest cooled by an external cooling means, (sea water, tower water or other means according to the cases), allowing the heat developed by the fermentation to be removed, and the temperature to be maintained at its optimum value.

The power necessary for the re-circulation is supplied by the same fermentation air and is imparted to the liquid mass of the liquor by the lifting action thereby exerted.

Figure 4:
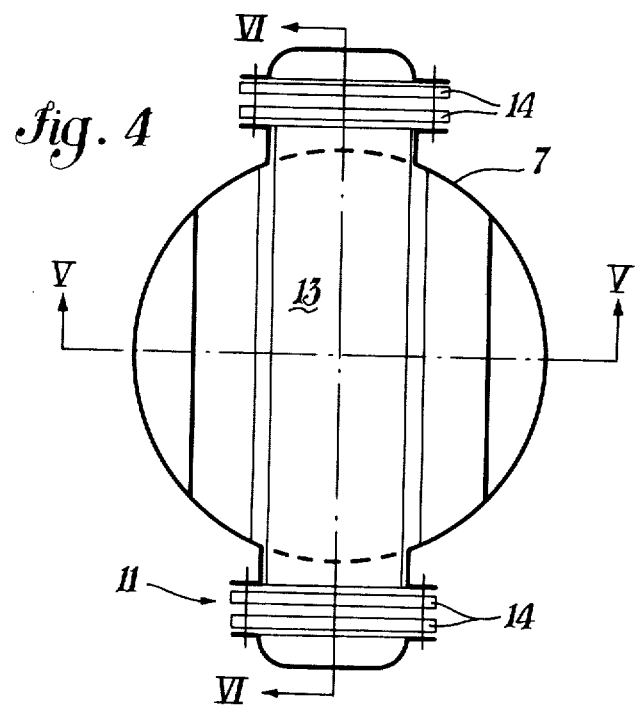
FIG. 4 shows the detail of the heat exchanger, in top plan view.
Figure 5:
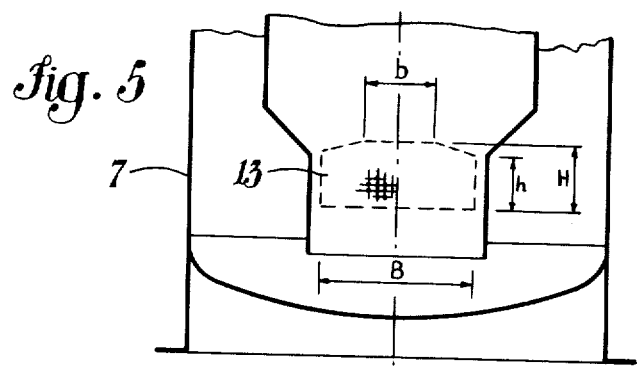
FIG. 5 is a cross sectional view taken along the plane V—V of FIG. 4.
Figure 6:
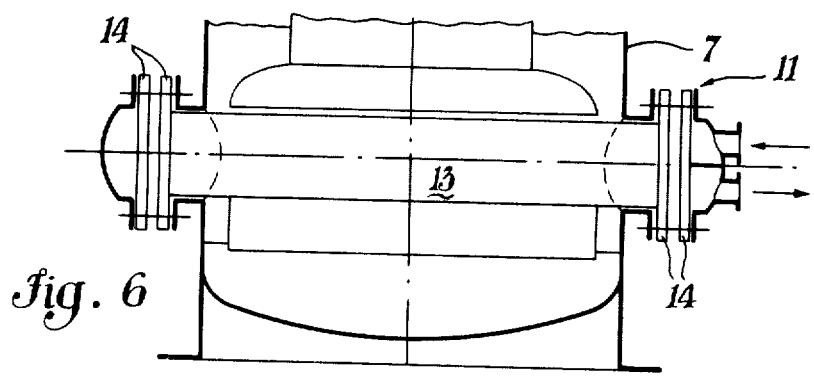
FIG. 6 is the cross sectional view taken along the plane VI—VI of FIG. 4.

The heat exchanger 11 is shown in detail in FIGS. 4, 5 and 6. It consists of a tube nest 13 directly immersed in the skirt 7 of the fermentor and closed at its ends by the terminal tube plates 14.

The heat exchanger 11 is located under the air distributor 12 in the zone comprised between the terminal parts of the two separating diaphragms 6 of the recirculation zones. The cross sectional shape of the tube nest is a trapezoid, in order to ensure a proper subdivision of the liquid flow through the nest. The contour of the cross section of the nest is defined by the values as follows (see FIG. 5):

| | |
|---|---|
| Width of the central part of the nest at constant height | b |
| total width of the nest | B |
| height of the nest at the ends | h |
| central height of the nest | H |

The tests demonstrated that the ratios as follows, between the above defined values, are the most convenient for ensuring a proper distribution of the flow:

$$0.3 \leq \frac{b}{B} \leq 1 \qquad 0.5 \leq \frac{h}{H} \leq 1$$

The material for manufacturing the tube nest 13 can be selected among the most various kinds of materials, depending upon the particular exigencies of the particular fermentation concerned and of the fluid used for cooling. In this connection, very useful proved to be the use of tubes made of titanium and other alloys allowing the direct use of sea water as refrigerating fluid.

Figure 7:
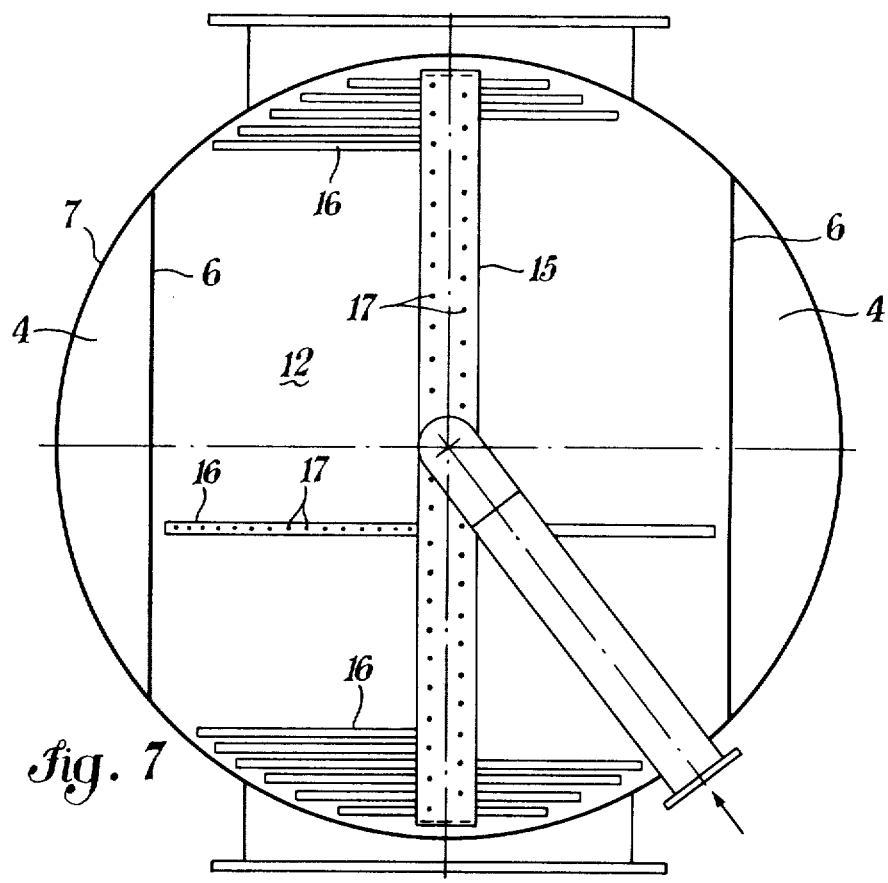
FIG. 7 shows the detail of the air distributor in top plan view.
Figure 8:
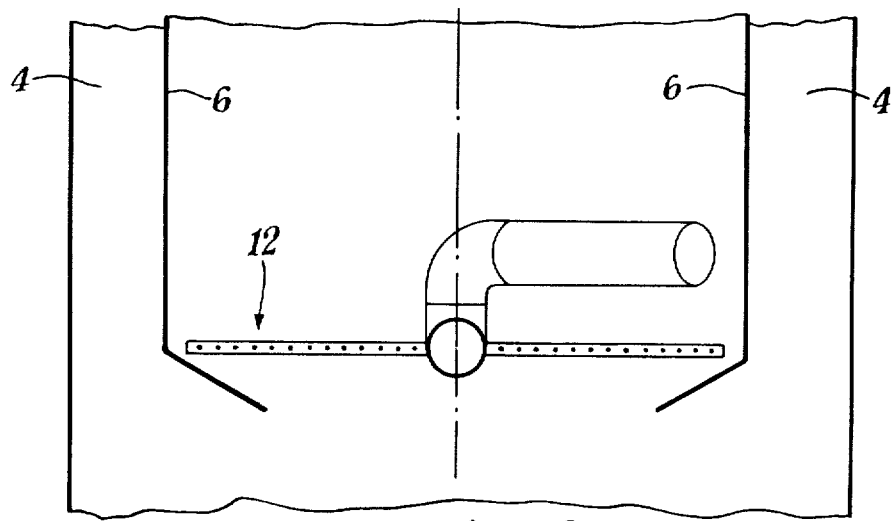
FIG. 8 shows the distributor of FIG. 7, in side elevational view.

The air distributor (FIGS. 7 and 8) is of a standard type, with a central manifold 15 and cross branches 16, and embodied so as to cover the entire cross sectional area of passage of the fermentation zone.

The outflow occurs through blowing nozzles 17 suitably distributed in the upper part of the manifold and of the cross branches.

The distribution of the blowing nozzles can be non-uniform, however so embodied as to obtain a greater aeration in correspondence with the central or lateral zones of the tube nest 13 in order to obtain the wanted subdivision of the flow through the tube nest itself.

As aforesaid, the fermentation zone is parted from the deaeration and recirculation zones by means of one or two parting diaphragms 6 located parallel to the axis of the fermentor and to the axis of the tube nest.

The inclination of the diaphragms can be varied along the height of the fermentor, departing thus from the vertical location, so as to embody, if required, a variable arrangement of both the fermentation zone and the gas-liquid separation and deaeration zones, in order to render optimum the size of the fermentor.

The present invention has been described in one preferred embodiment being however understood that constructive changes might be practically adopted without departing from the scope of the present industrial privilege.

Having thus described the present invention what is claimed is:

1. An air lift fermentor comprising a vessel including a hollow generally vertically disposed cylindrical body, a pair of spaced diaphragms located within said body and disposed generally longitudinally thereof and subdividing the interior of said body into a central fermentation zone and two lateral recirculation zones, said fermentation zone having an open lower end for receiving liquor to be fermented and said recirculating zones having upper and lower ends communicating with upper and lower ends of said fermentation zone for recirculating the liquor within said body, a heat exchanger mounted within a lower portion of said body, and an air distributor mounted within a lower portion of said fermentation zone for directing air substantially only into said fermentation zone.

2. A fermentor, as defined in claim 1, wherein said vessel includes an upper end dome having a wider cross-section than said cylindrical body and defining a separation zone for separating gas from the liquid, and said vessel further including a frusto-conical wall connecting said cylindrical body and said dome and defining together with said diaphragms a deaeration zone.

3. A fermentor, as defined in claim 1, wherein said heat exchanger includes a tube nest having a trapezoidal cross-sectional shape with its greater dimension located symmetrically with respect to the geometrical longitudinal axis of said fermentation zone.

4. A fermentor, as defined in claim 3, wherein said air distributor includes differentiated delivery means for optimizing flow of liquid through said tube nest.

5. A fermentor, as defined in claim 1, wherein said diaphragms are disposed for providing said zones with variable cross-sectional dimensions for promoting stirring in the fermentation zone and subsequent separation of gas from the liquid.

6. A fermentor, as defined in claim 1, wherein said heat exchanger includes tube means and head means comprising a tube plate, said tube plate being located externally with respect to said vessel so as to avoid any possibility of polluting the fermentation liquor and for allowing easy cleaning.

* * * * *